United States Patent

Shimomura et al.

[11] Patent Number: 6,077,288
[45] Date of Patent: Jun. 20, 2000

[54] VALVED TROCAR JACKET TUBE

[75] Inventors: Kazuyuki Shimomura, Tokyo; Yukihiko Tamai, Nagano-ken, both of Japan

[73] Assignee: Hakko Electric Machine Works Co., Ltd., Nagano-ken, Japan

[21] Appl. No.: 09/169,582

[22] Filed: Oct. 9, 1998

[30] Foreign Application Priority Data

Apr. 7, 1998 [JP] Japan .................................. 10-095077

[51] Int. Cl.$^7$ .................................................. A61B 17/34
[52] U.S. Cl. .......................... 606/185; 606/186; 604/167
[58] Field of Search ................... 606/185, 184, 606/186, 170; 604/167, 169, 245, 246, 247, 248, 320, 321, 323, 335, 336

[56] References Cited

U.S. PATENT DOCUMENTS 5,480,410  1/1996  Cuschieri et al. .
5,522,791  6/1996  Leyva .

FOREIGN PATENT DOCUMENTS

WO 95/07056  3/1995  WIPO .
WO 95/22289  8/1995  WIPO .
WO 98/48724  11/1998  WIPO .

*Primary Examiner*—Michael Buiz
*Assistant Examiner*—Lien Ngo
*Attorney, Agent, or Firm*—Scully, Scott, Murphy & Presser

[57] ABSTRACT

Disclosed is a valved trocar jacket tube, in which both ends of a first cylindrical elastic member are secured, one end of a second cylindrical elastic member is attached to one of first and second rings, which are so constructed that when they are rotated relatively in the opposite directions the opening of the first cylindrical elastic member is closed from the opening state, and a fluid container is provided at a predetermined position of the second cylindrical elastic member, which is inflated to have a ring shape by the increase of an inner pressure generated by injection of a fluid. According to this structure, it is possible to provide a valved trocar jacket tube, which can prevent leakage of an inert gas from an abdominal cavity without reducing the operativity during surgery.

7 Claims, 9 Drawing Sheets

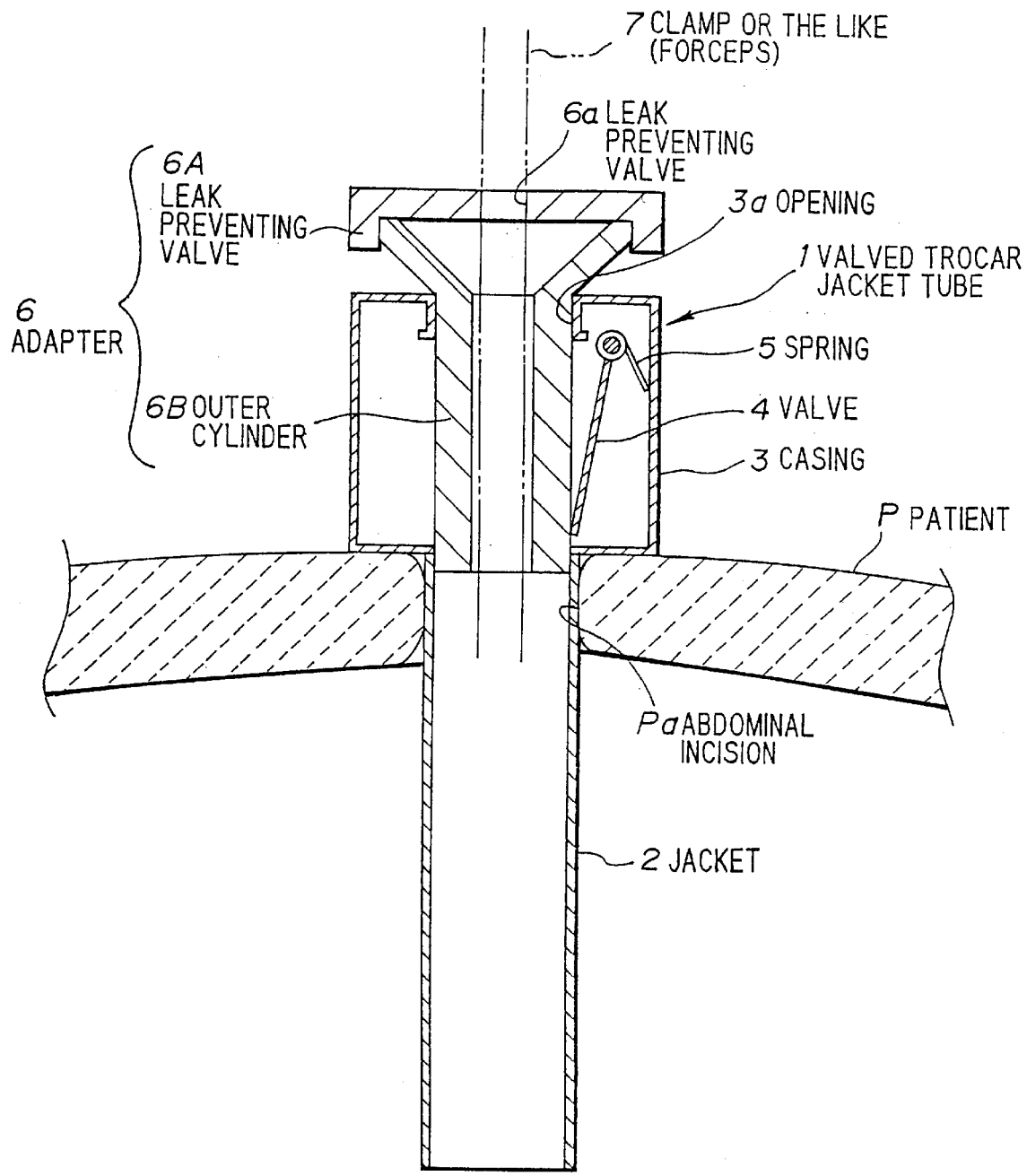

11b, 12b STEP PORTION
11 HALF RING
12 FEMAIL RING
111 CYLINDRICAL MEMBER

13a CYLINDRICAL SECTION
11A, 12A ENGAGE-GROOVE
113 AIR INJECTION INLET

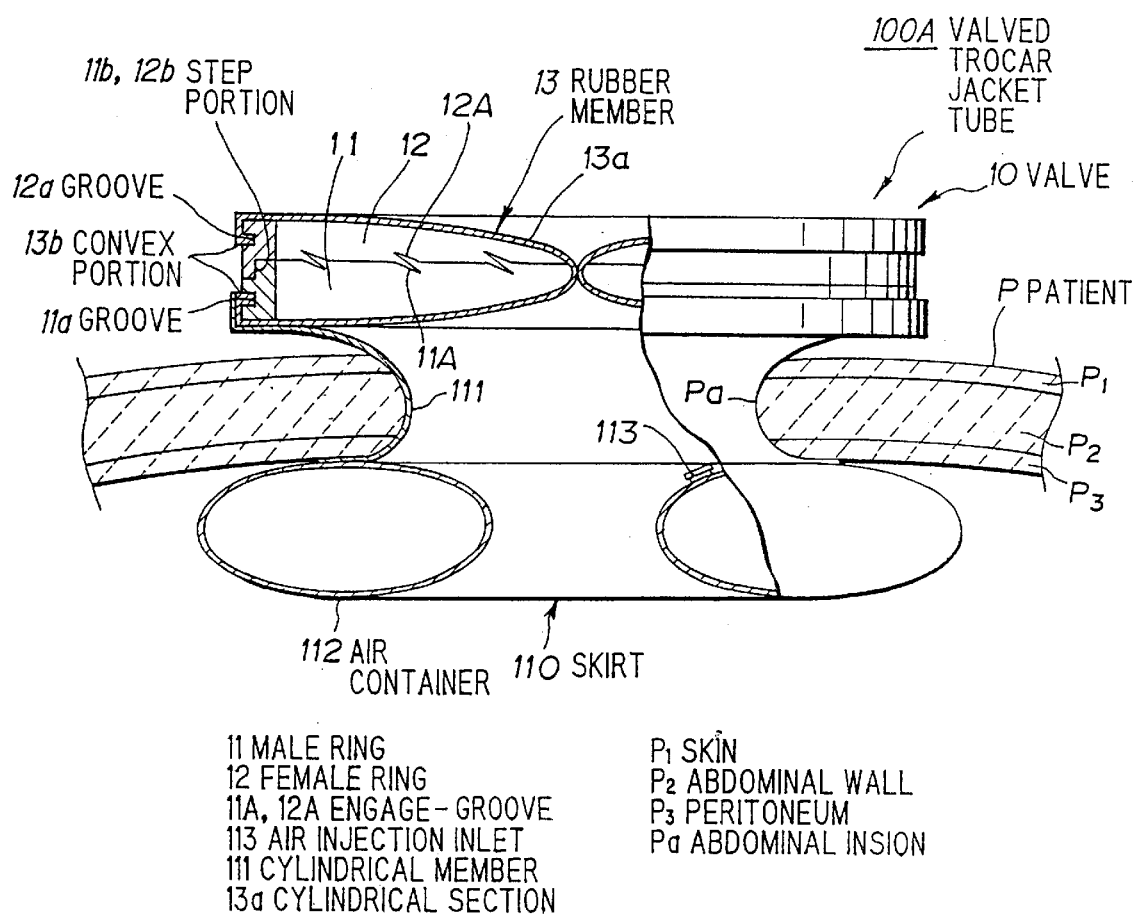

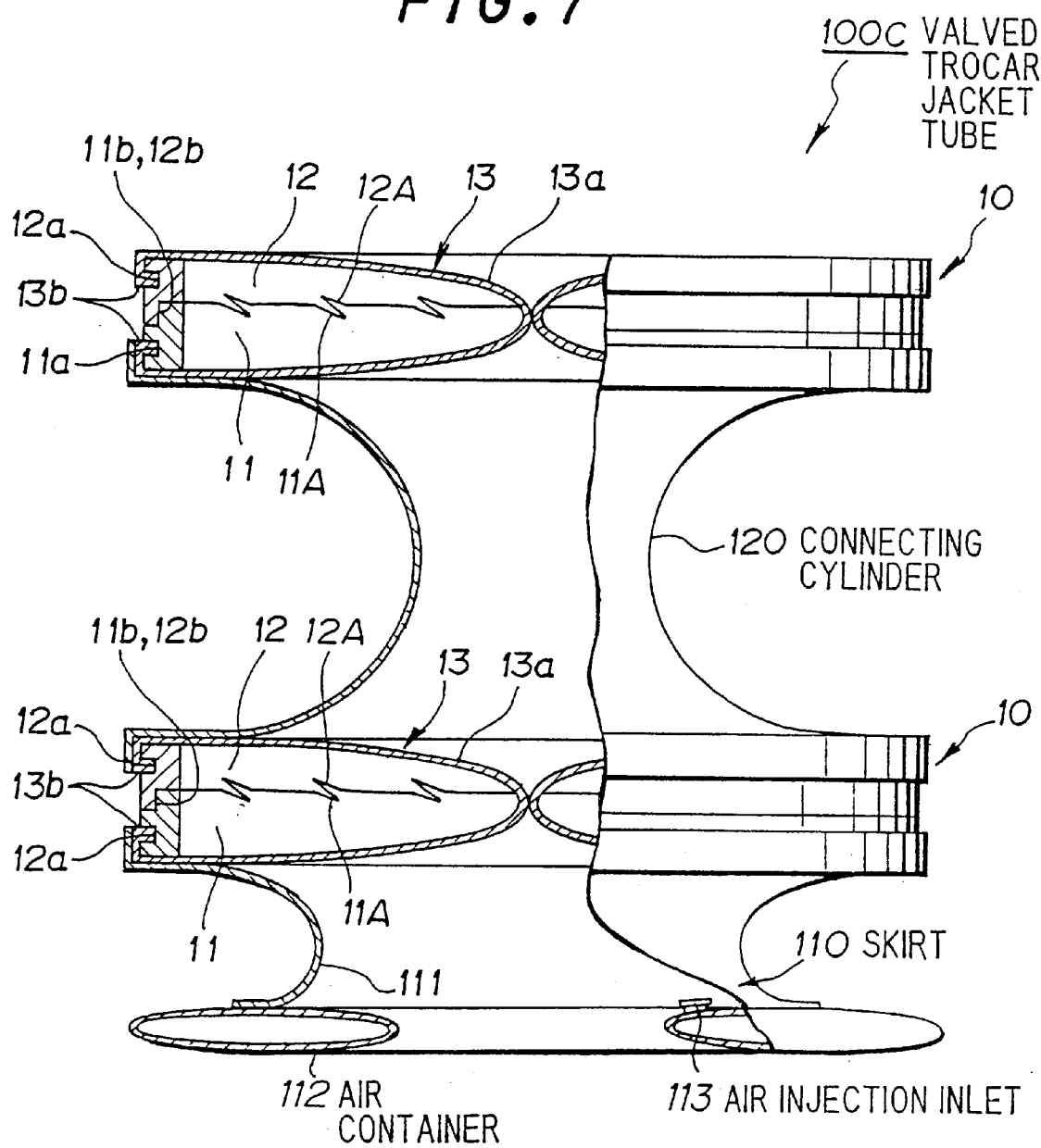

FIG. 8A

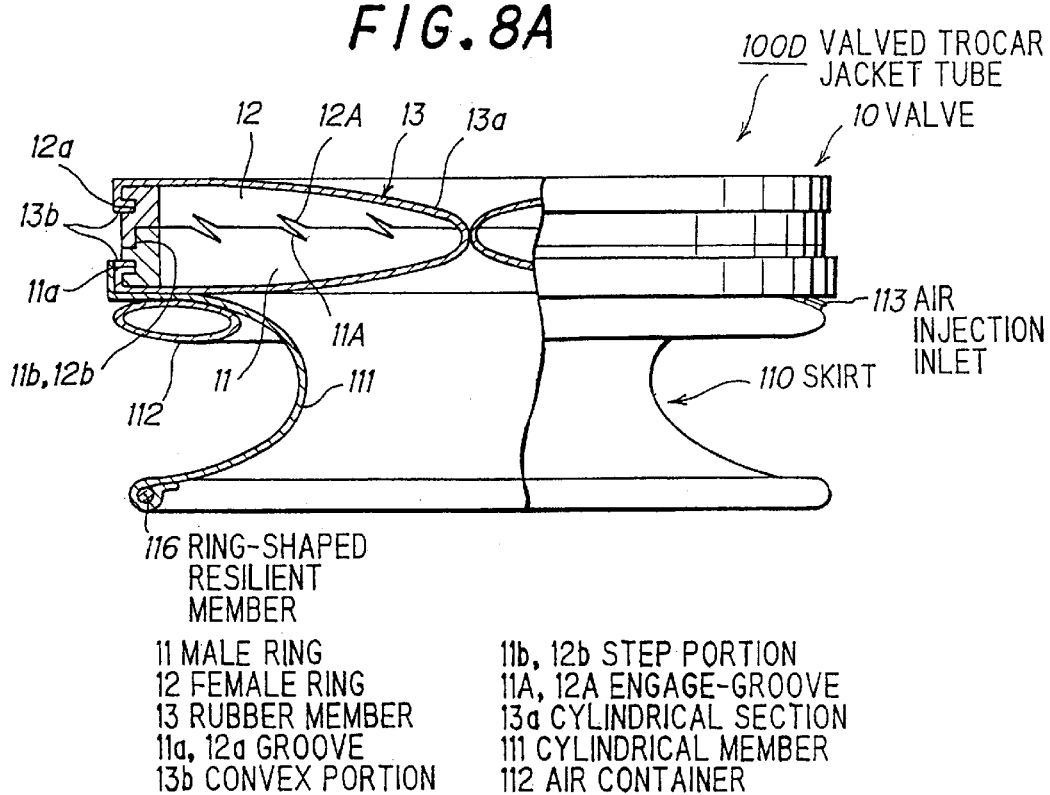

- 11 MALE RING
- 12 FEMALE RING
- 13 RUBBER MEMBER
- 11a, 12a GROOVE
- 13b CONVEX PORTION
- 11b, 12b STEP PORTION
- 11A, 12A ENGAGE-GROOVE
- 13a CYLINDRICAL SECTION
- 111 CYLINDRICAL MEMBER
- 112 AIR CONTAINER

100D VALVED TROCAR JACKET TUBE
10 VALVE
113 AIR INJECTION INLET
110 SKIRT
116 RING-SHAPED RESILIENT MEMBER

FIG. 8B

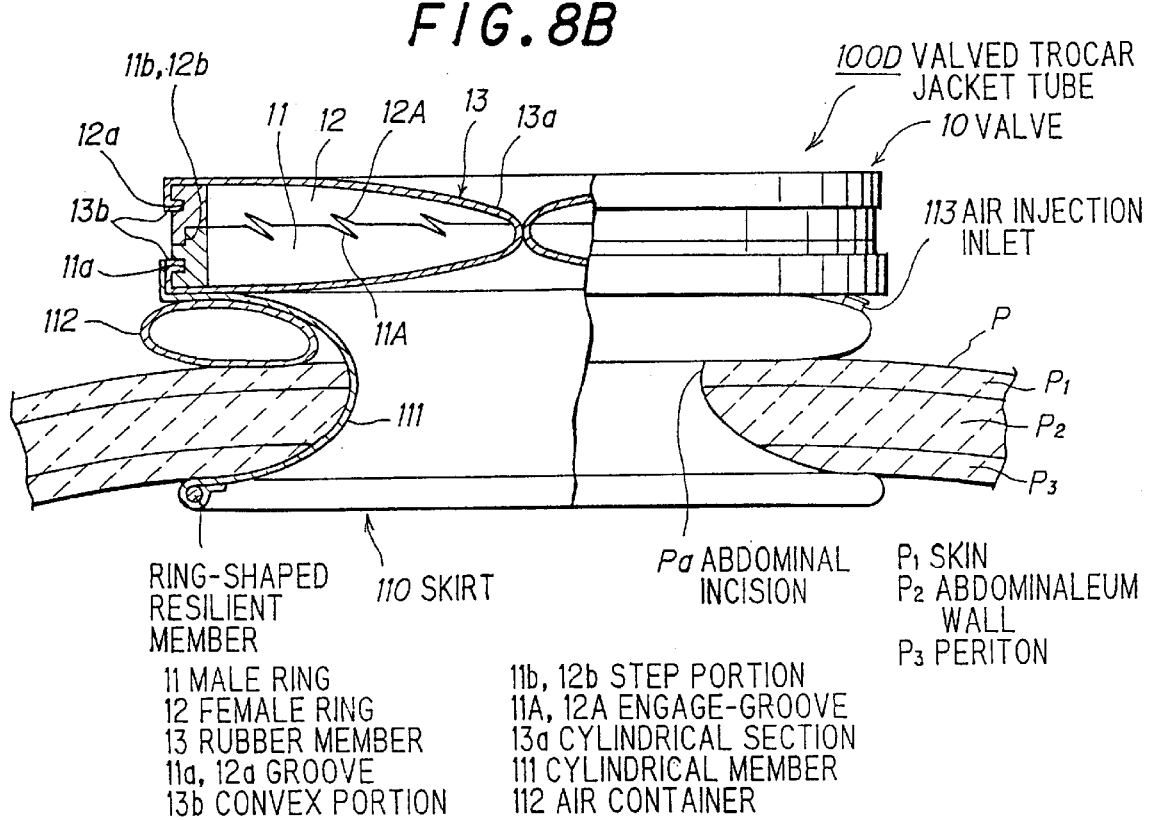

- 11 MALE RING
- 12 FEMALE RING
- 13 RUBBER MEMBER
- 11a, 12a GROOVE
- 13b CONVEX PORTION
- 11b, 12b STEP PORTION
- 11A, 12A ENGAGE-GROOVE
- 13a CYLINDRICAL SECTION
- 111 CYLINDRICAL MEMBER
- 112 AIR CONTAINER

100D VALVED TROCAR JACKET TUBE
10 VALVE
113 AIR INJECTION INLET
110 SKIRT
Pa ABDOMINAL INCISION
P1 SKIN
P2 ABDOMINALEUM WALL
P3 PERITON
RING-SHAPED RESILIENT MEMBER

VALVED TROCAR JACKET TUBE

FIELD OF THE INVENTION

The invention relates to a valved trocar jacket tube which is used in endoscopic surgery in pneumoperitoneum, and more particularly to a trocar jacket valve, which can prevent leakage of an inert gas from an abdominal cavity without decreasing operativity during the surgery.

BACKGROUND OF THE INVENTION

FIG. 1 shows a first conventional valved trocar jacket tube, wherein the conventional trocar jacket tube 1 comprises a cylindrical jacket 2 and a casing 3 secured to the top of the jacket 2. The casing 3 is provided with a circular opening 3a on the upper part thereof. Furthermore, the casing 3 contains a valve 4 for opening and closing the opening 3a on the inside thereof and a spring 5 for urging the valve 4 in the closing direction therein.

When the valved trocar jacket tube 1 thus constituted is employed, as shown in FIG. 2, the surgeon inserts the jacket 2 of the valved trocar jacket tube 1 into a site, for example, an abdominal incision Pa of a patient P being an object to be operated. In case of using a clamp (forceps) or the like 7, an adapter 6 called as reducer or introducer is used, which comprises a leakage preventing valve 6A having an opening 6a an inner diameter of which corresponds to an outer diameter of the clamp or the like 7 and an outer cylinder 6B. The surgeon sets the clamp or the like 7 having a diameter corresponding to the opening 6a of the adapter 6 thereto, and the adapter 6 is inserted through the opening 3a of the casing 3. In this case, the valve 4 is opened against the spring force of the spring 5 due to insertion of the adapter 6. As a result, leakage of an inert gas injected into an abdominal cavity for conducting easily endoscopy or the like is prevented.

According to the first conventional valved trocar jacket tube 1, however, there is a disadvantage in that since the diameter of the opening 3a provided on the casing 3 is constant, it is required to use an adapter 6 having the diameter corresponding to that of the clamp or the like 7 to be used, and the substitution to another adapter is troublesome, thereby preventing the operator's manipulation.

Further, there is another disadvantage in that since the standard sizes of the opening 6a of the adapter 6 are usually 5 mm, 10 mm, and 12 mm, a clamp or the like having an intermediate size such as 6 mm or 8 mm cannot be used, so that the sizes of the clamp or the like 7 are also restricted.

Still further, since the inner diameters of the openings 6a of the adapter 6 and the outer diameters of the clamp or the like 7 are nominal values, respectively, there is the other disadvantage in that the inner diameter of the opening 6a of the adapter 6 may not match with the outer diameter of the clamp or the like 7. As a result, it is impossible to use the clamp or the like 7 or it may cause leakage of the inert gas.

For solving these problems, the Applicant proposed a valved trocar jacket tube of another type in Japanese Patent Application No. 8-266883 (Japanese Patent Application Laid-Open No.10-108868) filed on Oct. 8, 1996, wherein the valved trocar jacket tube comprises a first cylindrical elastic member having an opening with a predetermined sectional area, a pair of rings, to which the ends of the first cylindrical elastic member are attached respectively, and which are so constructed that when they are rotated relatively in the opposite directions the opening of the first cylindrical elastic member is closed from the opening state, a second cylindrical elastic member to be inserted into an abdominal incision, one end of which is attached to one of the pair of rings, and a ring shaped elastic member provided at another end of the second cylindrical elastic member, which enlarges another end of the second cylindrical elastic member and contacts it closely to the abdominal incision.

According to the second conventional valved trocar jacket tube, when a pair of rings are rotated relatively in the opposite directions, an opening of a first cylindrical elastic member is closed due to the twist of the first cylindrical elastic member, so that it will fit securely and flexibly with the hands of the surgeon or the clamp or the like, which is preliminarily inserted into a incised portion of a diseased part through the opening. As a result, the types of clamps or the like to be employed are not limited and it is possible to use the clamps of the intermediate sizes or the clamps having contours other than a circular shape. Further, since the use of an adapter becomes unnecessary, it is not necessary to conduct substituting operation of the adapter, so that endoscopic surgery can be conducted smoothly. Still further, since the second cylindrical elastic member fits securely with an abdominal incision due to the tension thereof, the airtightness of an abdominal cavity can be kept and leakage of an inert gas from the abdominal cavity can be prevented.

On the other hand, U.S. Pat. No. 5,366,478 discloses a valved trocar jacket tube of the other type. This third conventional valved trocar jacket tube contains a pair of ring-shaped elastic members on the inside thereof and comprises a cylindrical air container having an opening provided at the central portion thereof, in which the opening section is changed to have a predetermined sectional area from the closed state due to injection of an air. This valved trocar jacket tube is such constructed that one of the pair of the ring-shaped elastic members is inserted into an abdominal cavity through an abdominal incision and air is injected into the cylindrical air container, so that the cylindrical air container fits securely to the abdominal incision.

According to the second conventional valved trocar jacket tube proposed by the Applicant, however, since the contacting force is determined in accordance with an outer diameter of the second cylindrical elastic member and the contour of the abdominal incision, when the contour of the abdominal incision becomes relatively large, the contact between the second cylindrical elastic member and the abdominal incision becomes insufficient, so that an inert gas is leaked from a gap defined by the second cylindrical elastic member and the abdominal incision.

On the other hand, according to the third conventional valved trocar jacket tube disclosed in U.S. Pat. No. 5,366,478, when the hand of the surgeon or the clamps or the like is inserted into an abdominal cavity or it is pull out therefrom, it is necessary to adjust the volume of an air injected into an air container. It is troublesome to conduct such an adjustment of the air volume for several times during the surgery, and it is impossible to avoid the leakage of an inert gas from the abdominal cavity at this time. Further, in view of decreasing the leakage of the inert gas to the minimum, if the air volume of the cylindrical air container is not reduced so much, the inserted hand or clamp or the like may scratch the cylindrical air container, and when the things come to the worst, it may be damaged.

SUMMARY OF THE INVENTION

Accordingly, it is an object of the invention to provide a valved trocar jacket tube, which can prevent leakage of an inert gas from an abdominal cavity without decreasing operativity during the surgery.

According to the first feature of the invention, a valved trocar jacket tube, comprises:

a first cylindrical elastic member having an opening with a predetermined sectional area;

closing means including a first ring for securing one end of the first cylindrical elastic member and a second ring for securing another end of the first cylindrical elastic member, the first and second rings rotating relatively in the opposite directions respectively for closing the opening from an opened state;

a second cylindrical elastic member, one end of which being attached to one of the first and second rings;

a ring member, which is elastically deformable and provided at another end of the second cylindrical elastic member; and a fluid container provided at an upper part of an outer side of the second cylindrical elastic member, which is inflated to have a ring shape by the increase of an inner pressure generated by injection of a fluid;

wherein:

the first cylindrical elastic member is positioned outside an incised portion of a diseased part and functions as a valve;.

the second cylindrical elastic member is positioned from outside to inside of the incised portion of the diseased part and maintains the incised portion at an opened state;

the ring member is positioned inside of the incised portion of the diseased part and engaged with the incised portion of the diseased part; and the fluid container is positioned outside the incised portion of the diseased part and fits securely the second cylindrical elastic member to side walls of the incised portion of the diseased part.

It is preferable that the fluid container is provided on the upper part of the outer side of the second cylindrical elastic member and detachable therefrom.

It is preferable that the closing means is connected to another closing means for closing an opening of a third cylindrical elastic member from an opened state.

According to the second feature of the invention, a valved trocar jacket tube, comprises:

a first cylindrical elastic member having an opening with a predetermined sectional area;

closing means including a first ring for securing one end of the first cylindrical elastic member and a second ring for securing another end of the first cylindrical elastic member, the first and second rings rotating relatively in the opposite directions respectively for closing the opening from an opened state;

a second cylindrical elastic member, one end of which being attached to one of the first and second rings; and a fluid container provided at an upper part of an outer side of the second cylindrical elastic member, which is inflated to have a ring shape by the increase of an inner pressure generated by injection of a fluid;

wherein:

the first cylindrical elastic member is positioned outside an incised portion of a diseased part and functions as a valve;

the second cylindrical elastic member is positioned from outside to inside of the incised portion of the diseased part and maintains the incised portion at an opened state; and the fluid container is positioned inside the incised portion of the diseased part and fits securely the second cylindrical elastic member to side walls of the incised portion of the diseased part.

It is preferable that the fluid container is bonded or fused to the another end of the second cylindrical elastic member.

It is preferable that the fluid container is constructed by piling a lower end of the second cylindrical elastic member to have a tube shape and bonding or fusing it to a predetermined portion of the second cylindrical elastic member.

It is preferable that the closing means is connected to another closing means for closing an opening of a third cylindrical elastic member from an opened state.

BRIEF DESCRIPTION OF THE DRAWINGS

The invention will be explained in more detail in conjunction with appended drawings, wherein:

FIG. 2 is a cross-sectional view showing a conventional valved trocar jacket tube as employed;

FIGS. 3A and 3B show a valved trocar jacket tube in a first preferred embodiment according to the invention, wherein FIG. 3A is a plan view thereof and FIG. 3B is a cross-sectional view thereof;

FIGS. 4A and 4B show the opened state of a valved trocar jacket tube in the first preferred embodiment according to the invention, wherein FIG. 4A is a plan view thereof and FIG. 4B is a cross sectional view thereof;

FIG. 5 is a cross-sectional view showing a valved trocar jacket tube as employed in the first preferred embodiment according to the invention;

FIG. 7 is a cross-sectional view showing a valved trocar jacket tube in a third preferred embodiment according to the invention;

FIGS. 8A and 8B show a valved trocar jacket tube in a fourth preferred embodiment according to the invention, wherein FIG. 8A is a cross-sectional view thereof and FIG. 8B is a cross-sectional view thereof as employed.

DESCRIPTION OF THE PREFERRED EMBODIMENTS

Next, a valved trocar jacket tube in the preferred embodiments according to the invention will be explained in detail as set out below.

Figure 1:
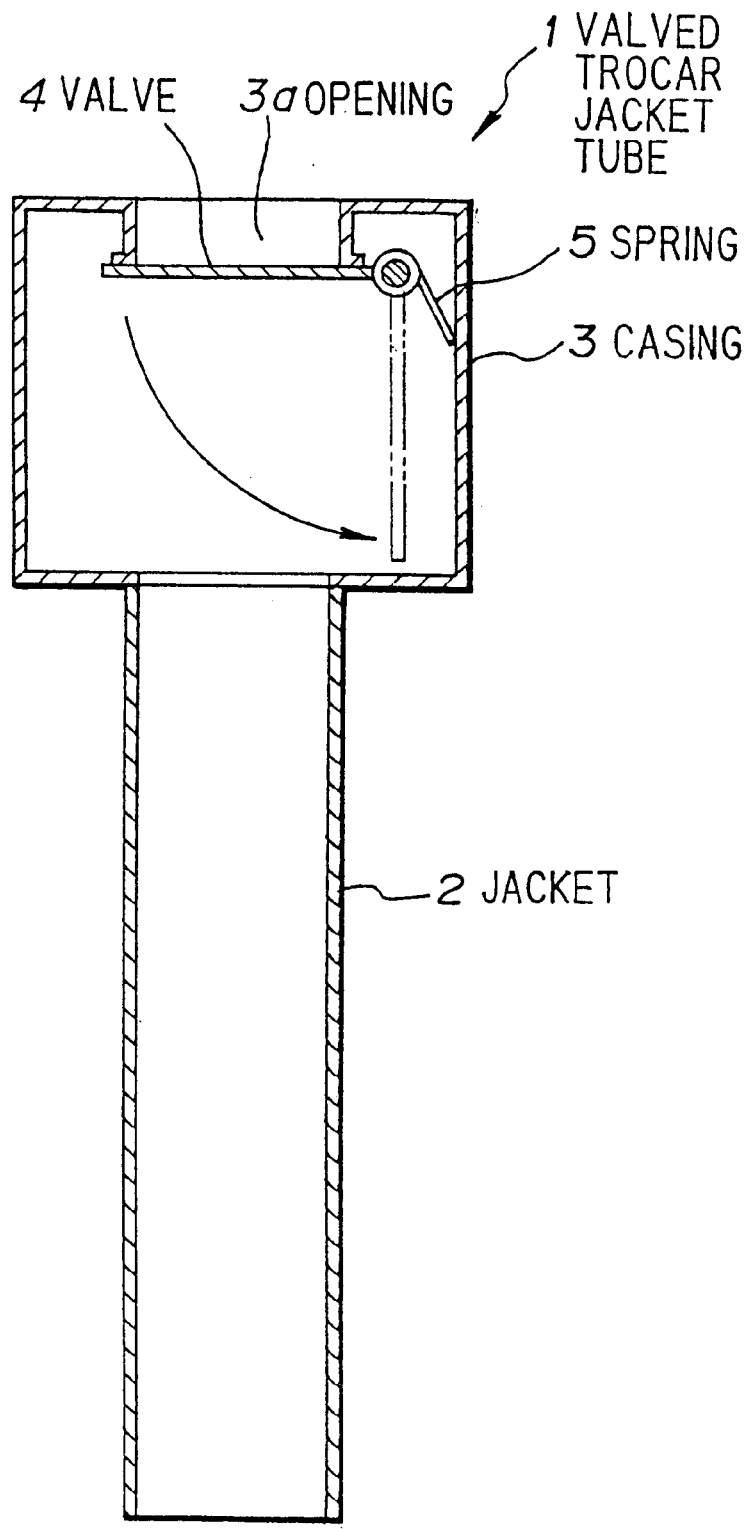
FIG. 1 is a cross-sectional view showing a conventional valved trocar jacket tube.
Figure 3A:
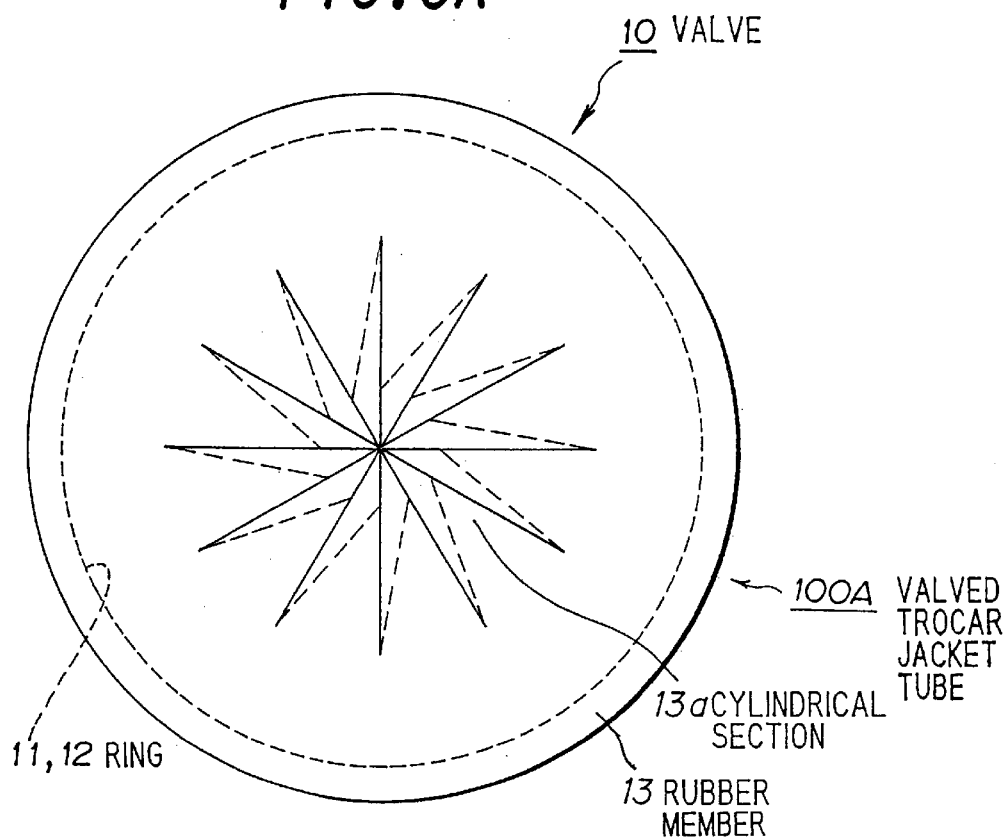
Figure 3B:
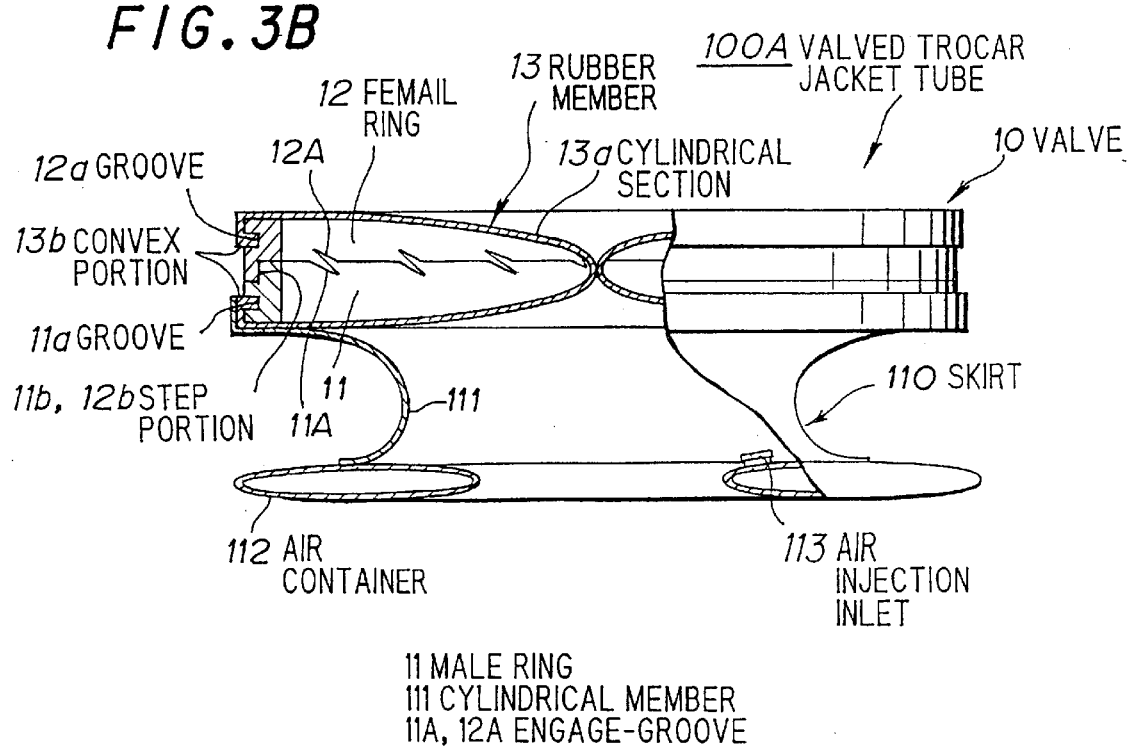

FIGS. 3A and 3B show a valved trocar jacket tube in a first preferred embodiment according to the invention, wherein a valved trocar jacket tube 100A comprises a valve 10 and a skirt 110 functioning as jacket means, and the skirt 110 is attached to the valve 10.

The valve 10 is composed of a pair of a male ring 11 and a female ring 12 placed oppositely to each other and a cylindrical rubber-like member 13 functioning as an elastic member the ends of which are attached to the pair of the rings 11 and 12, respectively.

The pair of rings 11 and 12 are prepared from a corrosion-resistant material such as metals, for example, stainless steel (SUS 304, 316, etc.), titanium, titanium alloys, aluminum, and aluminum alloys; ceramics; and high polymeric organic materials. Grooves 11a and 12a into which is fitted an end portion 13b of the rubber-like member 13 which will be explained hereafter are defined on the outer circumference of the pair of the rings 11 and 12, respectively. Furthermore, on the sides of the opposed pair of the rings 11 and 12 are defined step portions 11b and 12b being slid with each other. The pair of the rings 11 and 12 are arranged in such that they are rotatable relatively in the opposite directions due to the guiding action of the step portions 11b and 12b. Moreover, engage-grooves 11A and 12A are provided with faces contacting to each other of the pair of the rings 11 and 12, respectively, so that the rotation of the female ring 12 in the counter-clockwise direction is restricted by engaging force. The outer diameters of the pair of the rings 11 and 12 may be selected in response to the outer diameter of a member to be inserted into the valve 10. For example, it is preferred that the outer diameter thereof is around 100 mm in case of inserting an operator's hand into the valve, and it is around 30 mm in case of insertion of only a clamp (forceps) or the like. Moreover, the pair of rings 11 and 12 may be formed into somewhat elliptical shape, so that when either of the rings 11 or 12 is rotated at a predetermined angle in either direction, they are adapted to be braked.

The rubber-like member 13 is constituted in such that a cylindrical section 13a of the rubber-like member 13 is closed or opened when the pair of the rings 11 and 12 are relatively rotated in the opposite directions. More specifically, the rubber-like member 13 is formed from a thin film having a thickness of around 30 to 50 $\mu$m and made from a material having elasticity such as caoutchouc (natural rubber), synthetic rubber, polyvinyl chloride, silicone rubber, and a variety of elastomers. The rubber-like member 13 includes an opening 13c having a predetermined cross-sectional area at the central portion thereof, and is shaped in such that the diameter of which decreases in the direction from the opposite ends to the central opening 13c of the rubber-like member 13 (see FIG. 2). Furthermore, convex portions 13b which are fitted in the grooves 11a and 12a of the pair of the rings 11 and 12 are formed on the opposed ends of the rubber-like member 13, so that the rubber-like member 13 is detachable from the grooves 11a and 12a. Because of such detachable structure of the rubber-like member 13, it can be easily replaced by another rubber-like member 13 in the case when the used rubber-like member 13 is broken, etc.

Figure 4A:
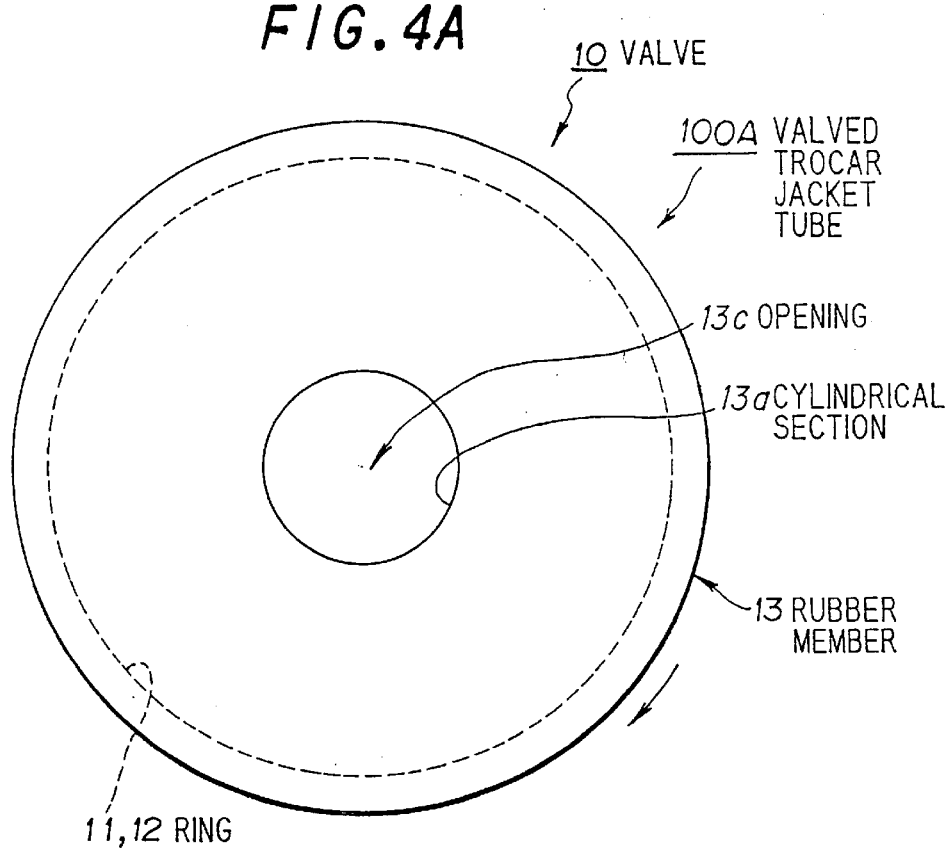
Figure 4B:
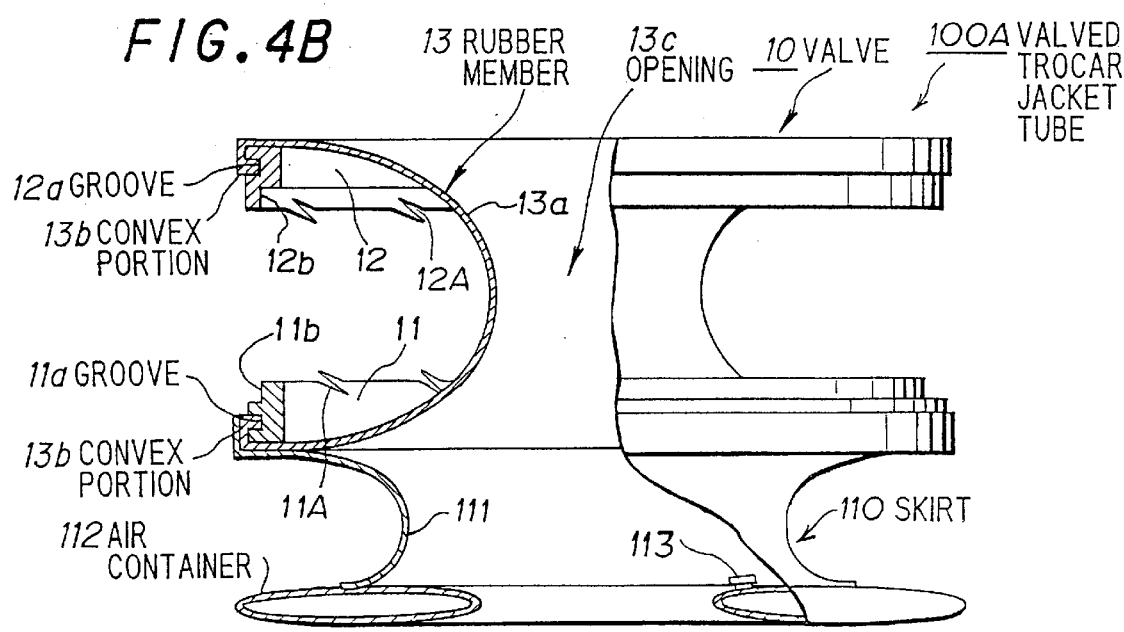

FIGS. 4A and 4B show an opened state of a cylindrical section 13a of the valve 10 for inserting a member to be inserted. When the female ring 12 is slightly rotated in the clockwise direction from the closed state of the cylindrical section 13a of the rubber-like member 13, so that the engaged state between the engage-groove 11A of the male ring 11 and the engage-groove 12A of the female ring 12 is released. Due to the resilient force of the rubber-like member 13, the female ring 12 is rotated at 180° in the counter clockwise direction, so that the cylindrical section 13a is opened and the pair of the rings 11 and 12 are separated from each other simultaneously, as shown in FIG. 4B. Further, when the female ring 12 is rotated at 180° in the clockwise direction against its resilient force, the pair of the rings 11 and 12 are joined with each other and the cylindrical section 13a is twisted to become a closed state as shown in FIGS. 4A and 4B. Next, while the step portion 11b of the male ring 11 and the step portion 12b of the female ring 12b are contacted with each other, the rotating force of the female ring 12 in the clockwise direction is released, so that the female ring 12 is rotated in the counter clockwise direction due to the resilient force of the rubber-like member 13. Then, the engage-groove 11A of the male ring 11 and the engage-groove 12A of the female ring 12 are engaged with each other, so that the state shown in FIGS. 4A and 4B is maintained.

The skirt 110 is composed of a cylindrical member 111 made of rubber or the like having the thickness of around 100 $\mu$m and a contour the diameter of which decreases from both the upper and lower ends towards a predetermined portion thereof, a ring-shaped air container 112 made of elastic material such as silicone rubber, etc., which is attached to the lower end of the cylindrical member 111 by bonding or fusion, and an air injecting inlet 113 which is provided with the air container 112 for injecting an air thereto and functions as a back-flow preventing valve for preventing the back-flow of the injected air. The upper end of the cylindrical member 111 is bonded or fused in vicinity of the convex portion 13b which is fitted into the groove 11b of the male ring 11 of the rubber-like member 13. Alternately, the upper end of the cylindrical member 111 may have such a constitution that it is fitted into the groove 11a of the male ring 11. By this structure, when the skirt 110 is broken, etc., it can be easily replaced by another new skirt 110.

FIG. 5 shows a valved trocar jacket tube 100A as used in the first preferred embodiment according to the invention, wherein $P_1$ is a skin of a patient P, $P_2$ is an abdominal wall of the patient P, and $P_3$ is a peritoneum of the patient P. For mounting the valved trocar jacket tube 100A, an air is injected into the air container 112 through the air injecting inlet 113 such that the air container 112 is inflated to have a desired outer diameter corresponding to the contour of an abdominal incision Pa. At this stage, the under side of the skirt 110 is inserted into the abdominal incision of the patient P while forcing the air container 112 to have a slender elliptical shape. Thereafter, the air container 112 is inflated into the circular configuration in an abdominal cavity to engage with the abdominal incision Pa as shown in FIG. 5. At this time, the cylindrical member 111 and an upper side of the air container 112 fit securely with a portion of the peritoneum $P_3$ of the abdominal incision Pa and the other portion of the peritoneum $P_3$ placed in the abdominal cavity, respectively. Then, the female ring 12 is slightly rotated in the clockwise direction from the closed state of the cylindrical section 13a of the rubber-like member 13, so that the engaged state between the engage-groove 11A of the male ring 11 and the engage-groove 12A of the female ring 12 is released. Due to the resilient force of the rubber-like member 13, the female ring 12 is rotated at 180° in the counter clockwise direction, and the cylindrical section 13a is opened. For using a clamp or the like, the surgeon inserts it into the abdominal cavity through the opened cylindrical section 13a and the cylindrical member 111.

According to the valved trocar jacket tube in the first preferred embodiment, the outer diameter of the air container 112 can be changed by adjusting the air volume existing in the air container 112, so that the outer diameter of the cylindrical member 111 can be adjusted in accordance with the contour of the abdominal incision Pa. Since the cylindrical member 111 fits securely with the peritoneum $P_3$ due to its tension, leakage of an inert gas from the abdominal incision Pa can be prevented regardless of the contour of the abdominal incision Pa. Further, as described in the background of the invention, when a hand or a clamp or the like is inserted into the abdominal cavity through the valve 10, the rubber-like member 13 fits securely with the hand or the clamp or the like, so that leakage of an inert gas from the valved trocar jacket tube 100A can be suppressed to the minimum.

Figure 6:
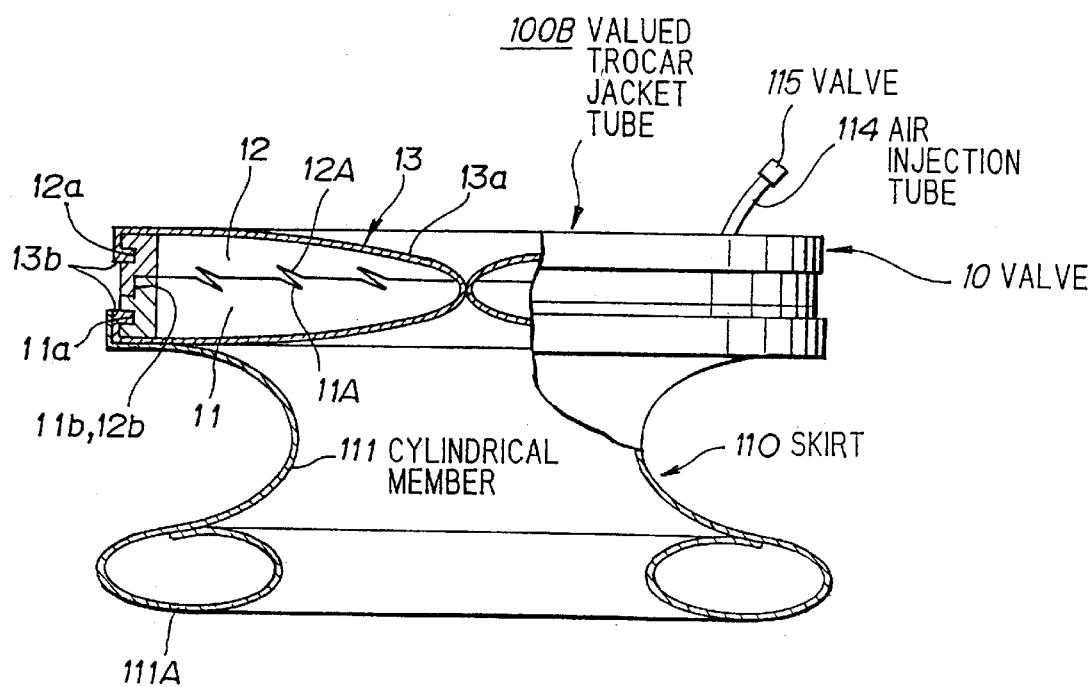
FIG. 6 is a cross-sectional view showing a valved trocar jacket tube in a second preferred embodiment according to the invention.

FIG. 6 shows a valved trocar jacket tube in the second preferred embodiment according to the invention, wherein a valved trocar jacket tube 100B comprises a tube 111A, which is formed by piling a lower end of a cylindrical member 111 of a skirt 110 inside to have a tube shape, and further bonding or fusing it to a predetermined portion of the cylindrical member 111. The tube 111A comprises an air injecting tube 114 introduced on the upper portion of the valve 10 and a valve 115 provided at the pointed end of the air injecting tube 114. An air is injected into the tube 111A through the valve 115 and the air injecting tube 114.

According to the valved trocar jacket tube in the second preferred embodiment, the same effects as in the first preferred embodiment can be obtained. Further, since the skirt 110 is composed of only the cylindrical member 111, the number of necessary parts can be reduced, so that the manufacturing cost of the device can be reduced. In the second preferred embodiment, air-injecting means can be provided in place of bonding or fusing the piled lower end of the cylindrical section 111.

FIG. 7 shows a valved trocar jacket tube in the third preferred embodiment according to the invention, wherein the valved trocar jacket tube 110C comprises upper and lower valves 10 placed opposite to each other, a connecting cylinder 120 for connecting the upper and lower valves 10, and a skirt 110 added to the lower valve which is similar to that in the first preferred embodiment. The upper end of the connecting cylinder 120 is bonded or fused in vicinity of the convex portion 13b which is fitted into the groove 11b of the male ring 11 contained in the upper valve 10, while the lower end of the connecting cylinder 120 is bonded or fused into the groove 12b of the female ring 12 contained in the lower valve 10. In the skirt 110, the upper end of the cylindrical member 111 is bonded or fused in vicinity of the convex portion 13b fitted into the groove 11b of the male ring 11 contained in the lower valve 10 as in the first preferred embodiment. The connecting cylinder 120 and the skirt 110 may be detachable from one another for facilitating the substitution thereof.

According to the valved trocar jacket tube in the third preferred embodiment, the upper valve 10 is firstly opened so as to insert an instrument(s) or a hand therethrough, and the upper valve is closed. Thereafter, the lower valve 10 is opened so as to insert the instrument(s) or a hand therethrough. In this case, even if the lower valve 10 is opened, since the gap defined by the inserted instrument(s) or hand is closed securely by the upper valve 10, leakage of the inert gas from the abdominal cavity as a result of application of pneumoperitoneum can be suppressed to the minimum.

FIG. 8A shows a valved trocar jacket tube in the fourth preferred embodiment according to the invention, wherein the valved trocar jacket tube 100D comprises a cylindrical member 111 composing a skirt 110, a circular ring-shaped elastic member 116 having an outer diameter of 100 mm which is attached to a lower end of the cylindrical member 111, a ring-shaped air container 112 bonded or fused to an upper end of the cylindrical member 111.

FIG. 8B shows the valved trocar jacket tube 100D as used in the fourth preferred embodiment. For mounting the valved trocar jacket tube 100D, the under side of the skirt 110 is inserted into an abdominal incision Pa of a patient P while forcing the ring-shaped elastic member 116 to have a slender elliptical shape. Thereafter, the ring-shaped elastic member 116 is expanded into a circular configuration in an abdominal cavity to engage with the abdominal incision Pa as shown in FIG. 8B. Thereafter, an air is injected into the air container 112 through the air injecting inlet 113 such that the air container is inflated to have desired contour and cross section respectively corresponding to the contour of the abdominal incision Pa and the total thickness of the skin $P_1$, the abdominal wall $P_2$, and the peritoneum $P_3$. At this time, since the skirt 110 is pulled and expanded by the air container 112, the cylindrical member 111 fits securely with the peritoneum $P_3$. When the female ring 12 is rotated at a predetermined angle, for example, 15° in either direction from the closed state of the cylindrical section 13a of the rubber-like member 13, the cylindrical section 13 is opened. For using the clamp or the like, the surgeon inserts the clamp or the like into the abdominal cavity through the opened cylindrical section 13a and the cylindrical member 111.

According to the valved trocar jacket tube 100D in the fourth preferred embodiment, the abdominal incision Pa can be securely held by injecting the air into the air container 112, so that the contact between the valved trocar jacket tube 100D and the skin $P_1$ can be improved. As a result, comparing to those in the first to third preferred embodiments, the valved trocar jacket tube 100D fits more securely with the abdominal incision Pa, so that the effect for preventing the leakage of the inert gas can be further improved. Further, since the volume of the air injected into the air container 112 can be changed in accordance with the contour of the abdominal incision Pa and the total thickness of the skin $P_1$, the abdominal wall $P_2$, and the peritoneum $P_3$, it is possible to apply the valved trocar jacket tube to more various patients and cases. Still further, since a space is provided around the air container 112 in the abdominal cavity, the surgeon can use this space to keep his hand beside, when the surgery is operated with inserting his hand into the abdominal cavity, so that it can facilitate the operation. In the fourth preferred embodiment, the air container 112 is secured to the skirt 110, however, it may be constructed to be detachable from the skirt 110.

Figure 9:
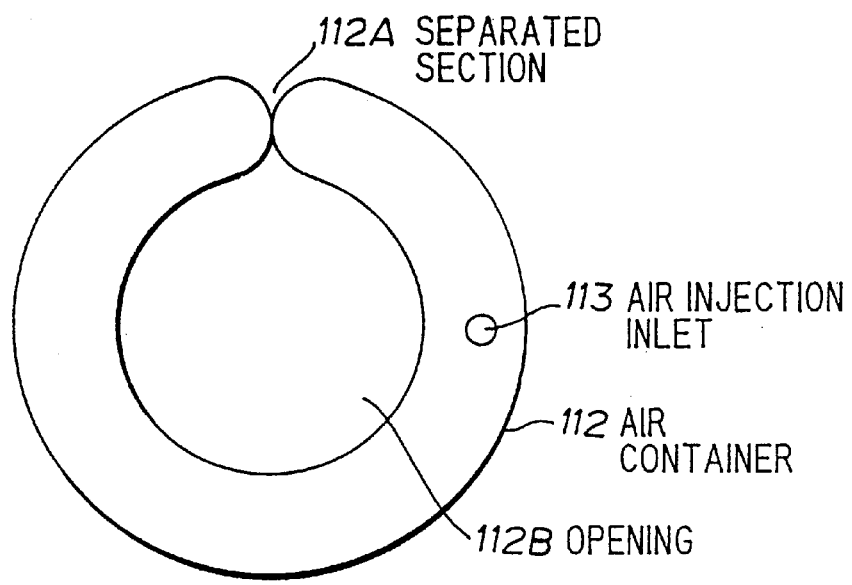
FIG. 9 is an explanatory diagram showing a variation of an air container in the fourth preferred embodiment according to the invention.

FIG. 9 shows an air container 112, which is constructed to be detachable from the valved trocar jacket tube 100D in the fourth preferred embodiment, wherein the air container 112 comprises a separated section 112A leading to an opening 112B. Herein, a cylindrical member 111 of a skirt 110 is inserted into the opening 112B through the separated section 112A and attached to an outer circumference of the cylindrical member 111 in practical use.

As a valved trocar jacket tube in the fifth preferred embodiment according to the invention, it is possible to provide a structure in which a valve 100 is added to an upper part of the valved trocar jacket tube 100D in the fourth preferred embodiment via a connecting cylinder 120 shown in FIG. 7.

As described above, in the valved trocar jacket tube according to the present invention, both ends of a first cylindrical elastic member are secured, one end of a second cylindrical elastic member is attached to one of first and second rings, which are so constructed that when they are rotated relatively in the opposite directions the opening of the first cylindrical elastic member is closed from the opening state, and a fluid container is provided at a predetermined position of the second cylindrical elastic member, which is inflated to have a ring shape by the increase of an inner pressure generated by injection of a fluid. According to this structure, it is possible to prevent leakage of an inert gas from an abdominal cavity without reducing the operativity during surgery.

Although the invention has been described with respect to specific embodiment for complete and clear disclosure, the appended claims are not to be thus limited but are to be construed as embodying all modification and alternative constructions that may be occurred to one skilled in the art which fairly fall within the basic teaching here is set forth.

What is claimed is:

1. A valved trocar jacket tube, comprising:

a first cylindrical elastic member having an opening with a predetermined sectional area;

closing means including a first ring for securing one end of said first cylindrical elastic member and a second ring for securing another end of said first cylindrical elastic member, said first and second rings rotating relatively in the opposite directions respectively for closing said opening from an opened state;

a second cylindrical elastic member, one end of which being attached to one of said first and second rings;

a ring member, which is elastically deformable and provided at another end of said second cylindrical elastic member; and a fluid container provided at an upper part of an outer side of said second cylindrical elastic member, which is inflated to have a ring shape by the increase of an inner pressure generated by injection of a fluid;

wherein:

said first cylindrical elastic member is positioned outside an incised portion of a diseased part and functions as a valve;

said second cylindrical elastic member is positioned from outside to inside of said incised portion of said diseased part and maintains said incised portion at an opened state;

said ring member is positioned inside said incised portion of said diseased part and engaged with said incised portion of said diseased part; and said fluid container is positioned outside said incised portion of said diseased part and fits securely said second cylindrical elastic member to side walls of said incised portion of said diseased part.

2. The valved trocar jacket tube, according to claim 1, wherein:

said fluid container is provided on said upper part of said outer side of said second cylindrical elastic member and detachable therefrom.

3. The valved trocar jacket tube, according to claim 1, wherein:

said closing means is connected to another closing means for closing an opening of a third cylindrical elastic member from an opened state.

4. A valved trocar jacket tube, comprises:

a first cylindrical elastic member having an opening with a predetermined sectional area;

closing means including a first ring for securing one end of said first cylindrical elastic member and a second ring for securing another end of said first cylindrical elastic member, said first and second rings rotating relatively in the opposite directions respectively for closing said opening from an opened state;

a second cylindrical elastic member, one end of which being attached to one of said first and second rings; and a fluid container provided at an upper part of an outer side of said second cylindrical elastic member, which is inflated to have a ring shape by the increase of an inner pressure generated by injection of a fluid;

wherein:

said first cylindrical elastic member is positioned outside an incised portion of a diseased part and functions as a valve;

said second cylindrical elastic member is positioned from outside to inside of said incised portion of said diseased part and maintains said incised portion at an opened state; and said fluid container is positioned inside of said incised portion said diseased part and fits securely said second cylindrical elastic member to side walls of said incised portion of said diseased part.

5. The valved trocar jacket tube, according to claim 4, wherein:

said fluid container is bonded or fused to said another end of said second cylindrical elastic member.

6. The valved trocar jacket tube, according to claim 4, wherein:

said fluid container is constructed by piling a lower end of said second cylindrical elastic member to have a tube shape and bonding or fusing it to a predetermined portion of said second cylindrical elastic member.

7. The valved trocar jacket tube, according to claim 4, wherein:

said closing means is connected to another closing means for closing an opening of a third cylindrical elastic member from an opened state.

* * * * *

UNITED STATES PATENT AND TRADEMARK OFFICE
CERTIFICATE OF CORRECTION

PATENT NO. : 6,077,288
DATED : June 20, 2000
INVENTOR(S) : Kazuyuki Shimomura

It is certified that error appears in the above-identified patent and that said Letters Patent are hereby corrected as shown below:

[73] Assignee:

Hakko Electric Machine Works, Co., Ltd., Nagano-ken, Japan
    Kazuyuki Shimomura, Tokyo, Japan Fig. 3B "femail" should read --female--
Fig. 4B "femail" should read --female--
Fig. 5 "insion" should read --incision--
Fig. 6 "valued" should read --valved--
Fig. 8B "abdominaleum" should read --abdominal--
Fig. 8B "periton" should read --peritoneum--

Signed and Sealed this

Twenty-fourth Day of April, 2001

*Attest:*

NICHOLAS P. GODICI

*Attesting Officer*      *Acting Director of the United States Patent and Trademark Office*